US00PP09755P

United States Patent [19]

Verhoeven

[11] Patent Number: Plant 9,755

[45] Date of Patent: Dec. 17, 1996

[54] IMPATIENS PLANT NAMED 'CHERRY ICE'

[75] Inventor: Thomas A. Verhoeven, Albany, Oreg.

[73] Assignee: D. S. Cole Growers, Inc., Loudon, N.H.

[21] Appl. No.: 527,210

[22] Filed: Sep. 12, 1995

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 8,340 8/1993 Verhoeven ..... Plt./87.6

P.P. 8,446 11/1993 Pfister ..... Plt./87.6

P.P. 92,869 9/1995 Cole ..... Plt./87.6

*Primary Examiner*—James R. Feyrer

*Attorney, Agent, or Firm*—Proprietary Rights International

[57] ABSTRACT

A distinct cultivar of Impatients plant named Cherry Ice, characterized by its consistently double, deep red flowers; uniform plant habit; freely branching habit; variegated foliage with green centers surrounded by a white edges; early flowering; and floriferousness.

2 Drawing Sheets

The present invention relates to a new and distinct cultivar of Impatiens plant, botanically known as *Impatiens walleriana,* and hereinafter referred to by the cultivar name Cherry Ice.

The new cultivar was discovered by the inventor as a sport or mutation of the nonpatented Impatiens cultivar Rosebud™ Red, in approximately August, 1994, in greenhouses in Albany, Oreg.

Asexual reproduction of the new cultivar by terminal cuttings taken at Albany, Oreg. and Loudon, N.H., has shown that the unique features of this new Impatiens are stabilized and reproduced true to type in successive generations.

The following traits have been repeatedly observed and are determined to be the unique characteristics of the new Impatiens. These characteristics in combination distinguish Cherry Ice as a new and distinct cultivar:

1. Consistently double, deep red flowers.
2. Uniform plant habit, plants are mounded in shape.
3. Freely branching habit.
4. Variegated foliage. Foliage is normally green in the center surrounded by distinct white edges. Variegation is white and does not show signs of yellowing as leaves mature.
5. Early flowering. Plants commence flowering approximately five to seven weeks after planting.
6. Floriferousness, plants are continuously covered with flowers.

Compared to its parent the new Impatiens has green and white variegated foliage whereas the foliage of the cultivar Rosebud™ Red is solid green without variegation. The new Impatiens is more freely branching and therefore has a more dense growth habit compared to the cultivar Rosebud™Red. Moreover, the new Impatiens is less vigorous than the cultivar Rosebud™ Red.

The new Impatiens can also be compared to the patented cultivar Blackberry Ice (U.S. Plant Pat. No. 8,340). Both cultivars are generally similar in foliage variegation and growth habit, however, the flower color of the new Impatiens is deep red compared to the red-purple flower color of the cultivar Blackberry Ice. Additionally, the green base foliage color appears to be darker on plants of the new Impatiens compared to plants of the cultivar Blackberyy Ice.

The accompanying colored photographs illustrate the overall appearance of the new cultivar, showing the colors as true as it is reasonably possible to obtain in colored reproductions of this type.

The first photograph comprises a front view of a typical hanging basket plant of the new Impatiens grown in Loudon, N.H.

The second photograph comprises a close-up view of the flowers and variegated leaves of the new Impatiens grown in Loudon, N.H.

The cultivar Cherry Ice has not been observed under all possible environmental conditions. The phenotype may vary somewhat with variations in environment such as temperature, daylength and light intensity, without, however, any variance in genotype.

The following observations, measurements and comparisons describe plants grown in Albany, Oreg., and Loudon, N.H., under commercial practice in a greenhouse. In the description, color references are made to The Royal Horticultural Society Colour Chart except where general terms of ordinary dictionary significance are used. The color values were determined during sunny to partly cloudy conditions at approximately 11:00 a.m. under part natural and part fluorescent light in Loudon, N.H.

Botanical classification: *Impatiens walleriana* cultivar Cherry Ice.

Parentage:

Naturally-occurring mutation of *Impatiens walleriana* cultivar Rosebud™ Red.

Propagation:

*Type cutting.*—Terminal cuttings.

*Time to initiate roots.*—7 days at 21C soil temperature.

*Rooting habit.*—Numerous, fibrous, and well-branched.

PLANT DESCRIPTION

Form: Mounded form, spreading and arching.

Growth habit: Less vigorous than non-variegated Impatiens. Freely branching, dense growth. Suitable for 10 to 25-cm containers. Under optimal environmental conditions, eight to ten weeks are required to produce proportional 12.5-cm potted plants that are 12.5 to 15 cm in height and 15 to 18 cm in diameter.

Foliage description: Leaves simple, generally symmetrical, abundant. Variegation is comprised of three colors or shades: solid green, green with a silver sheen, and a white edge which varies in width, all comprising varying percentages of leaf area.

*Size.*—Length: 3 to 5 cm. Width: 2.5 to 3 cm.

*Shape.*—Ovate with acuminate tip.

*Texture.*—Smooth with some wrinkling.

*Margin.*—Slightly serrated.

*Color.*—Top side: 137A-B overlaid with shiny white-gray on surface providing a gray-green overall effect that is darker green than 191A-B. Green center surrounded by edge of 11C-D. On immature foliage, edge variegation of 11C-D expands inwardly towards midrib in varying degrees as foliage maturs. Under side: 138C surrounded by margin of 11C-D with spotted red coloring, faded 53D. Differences in variegation patterns are visible in the photographs.

*Venation.*—Not distinctive.

Flower Description

Flower type and habit: Consistently double flowers. Freely and continuously flowering. Flower buds are spherical and open similar to a rose in fullness. The flowers open slightly above or even with the foliage, arising from leaf axils, three to five flowers per axil, terminal bud opening first.

Time to flower: Flowering generally commences five to seven weeks after planting.

Flowering season: Year-round under greenhouse conditions, optimal flowering during spring season in northern hemisphere.

Flower diameter: 3 to 5 cm.

Flower buds:

*Shape.*—Spherical.

*Color.*—Generally white with a slight touch of green.

Petals:

*Shape.*—Round to slightly oblong with indentation at tip.

*Quantity.*—At least 25 per flower.

*Color.*—Upper side, mature: 53B with a white, 155D, center eye 2 to 3 mm from base. Under side, mature: Between 55A-B and 47D. Fade: Flower color fades to 53D.

Spur:

*Shape.*—Narrow and curved.

*Quantity.*—One per flower.

*Length.*—1.5 cm.

*Color.*—Varies from a generally transparent light green (no corresponding R.H.S. color value) to a salmon/pink color, 35D, when flower is fully mature.

Reproductive organs: None observed.

Disease Resistance:

Some resistance to Botrytis. Root fungi are seldom a problem.

It is claimed:

1. A new and distinct cultivar of Impatiens plant named Cherry Ice, as illustrated and described.

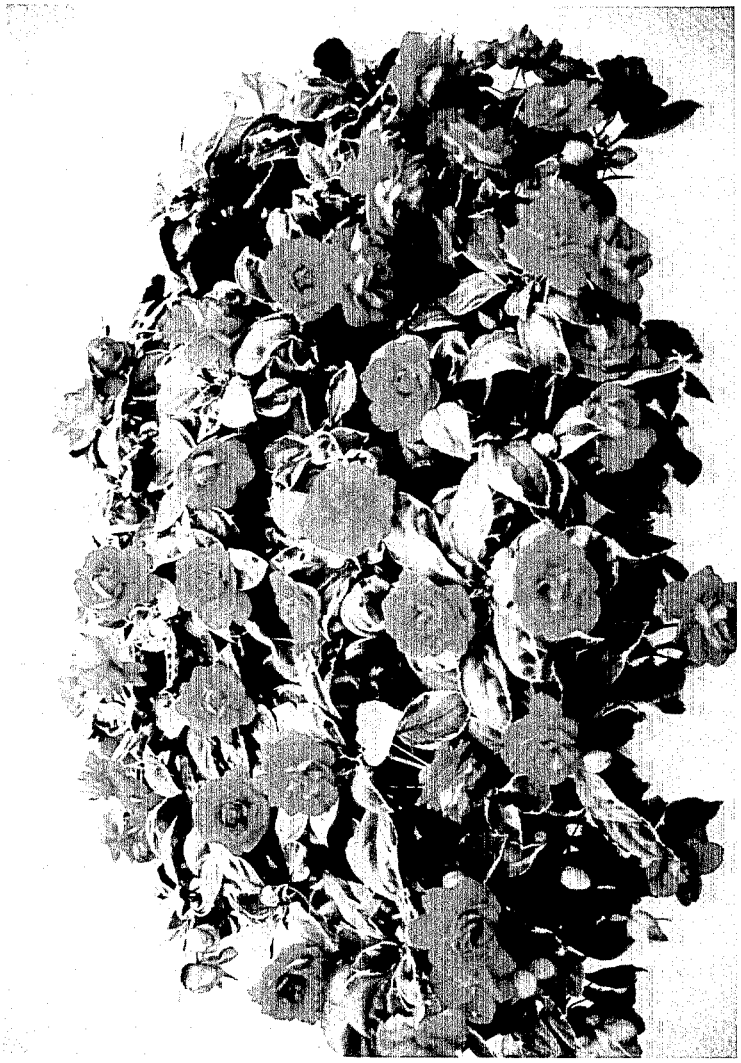

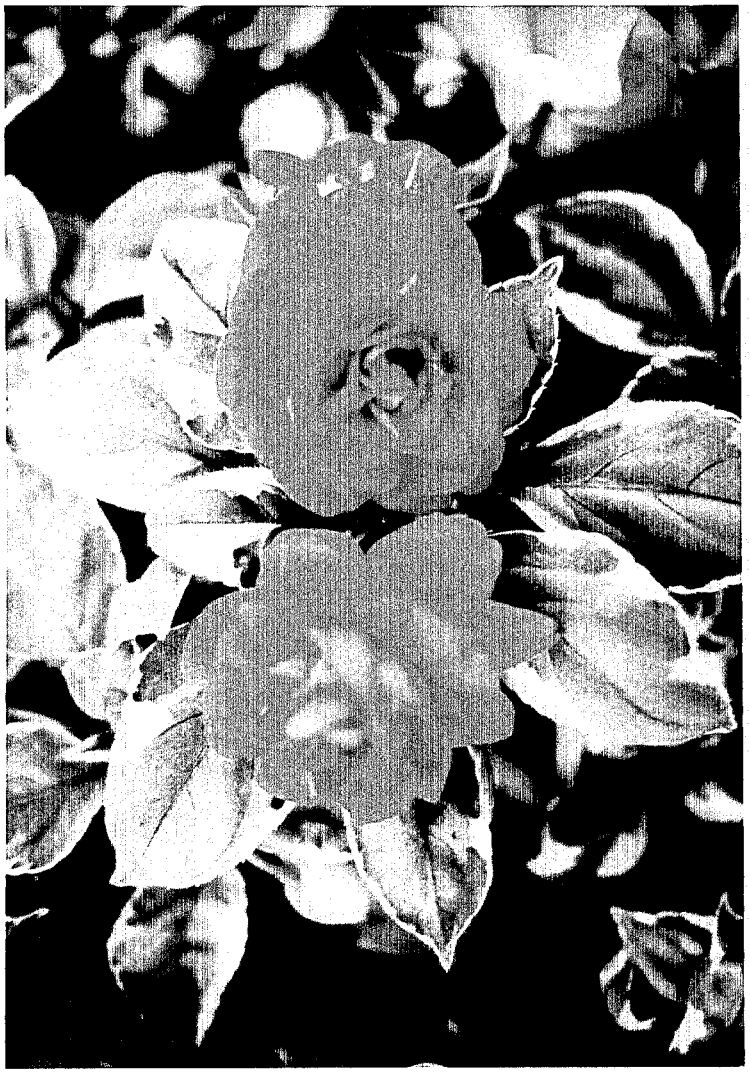

* * * * *